(12) United States Patent
Zeman

(10) Patent No.: US 7,239,909 B2
(45) Date of Patent: Jul. 3, 2007

(54) IMAGING SYSTEM USING DIFFUSE INFRARED LIGHT

(75) Inventor: Herbert D. Zeman, Memphis, TN (US)

(73) Assignee: Luminetx Technologies Corp., Memphis, TN (US)

( * ) Notice: Subject to any disclaimer, the term of this patent is extended or adjusted under 35 U.S.C. 154(b) by 423 days.

(21) Appl. No.: 10/386,249

(22) Filed: Mar. 11, 2003

(65) Prior Publication Data
US 2004/0111030 A1   Jun. 10, 2004

Related U.S. Application Data

(63) Continuation-in-part of application No. 09/487,007, filed on Jan. 19, 2000, now Pat. No. 6,556,858.

(51) Int. Cl.
*A61B 6/00*   (2006.01)

(52) U.S. Cl. .............. 600/473; 600/310; 600/407; 600/475; 600/476; 324/36; 345/1.1; 345/30; 250/226; 250/330; 250/331; 250/332; 250/333; 250/334; 250/341.8

(58) Field of Classification Search ........... 600/473, 600/476, 470, 310
See application file for complete search history.

(56) References Cited

U.S. PATENT DOCUMENTS

| | | | |
|---|---|---|---|
| 3,693,025 A | 9/1972 | Brunton | 250/83.3 H |
| 3,892,492 A | 7/1975 | Eichenberger | 356/199 |
| 4,699,149 A | 10/1987 | Rice | 128/664 |
| 4,817,622 A * | 4/1989 | Pennypacker et al. | 600/473 |
| 4,893,223 A | 1/1990 | Arnold | 362/252 |
| 4,908,876 A | 3/1990 | DeForest et al. | |
| 4,945,253 A | 7/1990 | Frohardt | 250/571 |
| 4,947,850 A | 8/1990 | Vanderkooi et al. | |
| 5,041,965 A | 8/1991 | Chen | |
| 5,073,714 A | 12/1991 | Nguyen | 250/341 |
| 5,087,822 A | 2/1992 | Fairlie et al. | 250/572 |

(Continued)

FOREIGN PATENT DOCUMENTS

EP   1 065 969   6/2002

(Continued)

OTHER PUBLICATIONS

H.D. Zeman, G. Lovhoiden, and H Deshmukh: Design of a Clinical Vein Contrast Enhancing Projector, Proc. of SPIE, vol. 4254, pp. 204-215, Jun. 2001.

(Continued)

*Primary Examiner*—Brian L. Casler
*Assistant Examiner*—William Jung
(74) *Attorney, Agent, or Firm*—Butler, Snow, O'Mara, Stevens & Canada, PLLC

(57) ABSTRACT

An imaging system illuminates body tissue with infrared light to enhance visibility of subcutaneous blood vessels, and generates a video image of the body tissue and the subcutaneous blood vessels based on reflected infrared light. The system includes an infrared light source for generating the infrared light and a structure for diffusing the infrared light. The diffusing structure includes one or more layers of diffusing material for diffusing the light. The system further includes a video imaging device for receiving the infrared light reflected from the body tissue and for generating a video image of the body tissue based on the reflected infrared light.

26 Claims, 12 Drawing Sheets

U.S. PATENT DOCUMENTS

| | | | | |
|---|---|---|---|---|
| 5,159,361 | A * | 10/1992 | Cambier et al. | 351/212 |
| 5,185,638 | A | 2/1993 | Conzola et al. | 356/237 |
| 5,231,434 | A | 7/1993 | Kennedy et al. | |
| 5,353,075 | A | 10/1994 | Conner et al. | |
| 5,359,550 | A | 10/1994 | Chen | |
| 5,367,439 | A | 11/1994 | Mayer et al. | 362/32 |
| 5,424,838 | A | 6/1995 | Siu | |
| 5,477,332 | A | 12/1995 | Stone et al. | 356/371 |
| 5,497,266 | A * | 3/1996 | Owen | 359/353 |
| 5,514,864 | A | 5/1996 | Mu-Tung et al. | 250/205 |
| 5,519,208 | A * | 5/1996 | Esparza et al. | 250/226 |
| 5,543,865 | A * | 8/1996 | Nanjo | 351/206 |
| 5,608,210 | A | 3/1997 | Esparza et al. | |
| 5,678,555 | A | 10/1997 | O'Connell | 128/664 |
| 5,757,544 | A | 5/1998 | Tabata et al. | |
| 5,772,593 | A * | 6/1998 | Hakamata | 600/407 |
| 5,787,185 | A | 7/1998 | Clayden | 382/115 |
| RE36,044 | E | 1/1999 | Benaron | 600/310 |
| 5,907,395 | A | 5/1999 | Schulz et al. | |
| 5,947,906 | A | 9/1999 | Dawson, Jr. et al. | |
| 5,969,754 | A | 10/1999 | Zeman | |
| 6,101,038 | A * | 8/2000 | Hebert et al. | 359/618 |
| 6,178,340 | B1 * | 1/2001 | Svetliza | 600/310 |
| 6,219,572 | B1 | 4/2001 | Young | 600/431 |
| 6,230,046 | B1 | 5/2001 | Crane et al. | 600/476 |
| 6,251,100 | B1 | 6/2001 | Flock et al. | 606/2 |
| 6,314,311 | B1 | 11/2001 | Williams et al. | 600/425 |
| 6,353,753 | B1 | 3/2002 | Flock et al. | 600/473 |
| 6,374,128 | B1 | 4/2002 | Toida et al. | 600/310 |
| 6,433,760 | B1 | 8/2002 | Vaissie et al. | 345/8 |
| 6,438,396 | B1 | 8/2002 | Cook et al. | 600/310 |
| 6,464,646 | B1 | 10/2002 | Shalom et al. | 600/549 |
| 6,556,858 | B1 * | 4/2003 | Zeman | 600/473 |
| 6,574,432 | B2 * | 6/2003 | Nanjyo | 396/18 |
| 6,650,916 | B2 | 11/2003 | Cook et al. | 600/322 |
| 6,813,010 | B2 | 11/2004 | Kono | 356/71 |
| 2004/0022421 | A1 | 2/2004 | Endoh et al. | |
| 2004/0064057 | A1 * | 4/2004 | Siegel | 600/500 |

FOREIGN PATENT DOCUMENTS

| | | |
|---|---|---|
| JP | 2172472 | 7/1990 |
| JP | 2172473 | 7/1990 |
| JP | 2174852 | 7/1990 |
| JP | 2174853 | 7/1990 |
| JP | 2174854 | 7/1990 |
| WO | 99/48420 | 3/1997 |
| WO | 97/08537 | 9/1999 |

OTHER PUBLICATIONS

H.D. Zeman, G. Lovhoiden, and H Deshmukh: Optimization of Subcutaneous Vein Contrast Enhancement, Proc. of SPIE, vol. 3911, pp. 50-57, May 2000.

H.D. Zeman and G. Lovhoiden: Enhancing the Contract of Subcutaneous Veins. Proc. of SPIE, vol. 3595, pp. 219-230, Jul. 1999.

H. Deshmukh: Vein Contrast Enhancement Using Diffuse Infrared Light, Masters Thesis, University of Tennessee, Health Science Center, 2002.

Peli et al., Image Enhancement for the Visually Impaired, Investigative Opthamology & Visual Science, vol. 32, No. 8, Jul. 1991, pp. 2337-2350.

In Focus Systems, LitePro 620, http://www.infocus.com/products/projectors/1p620.html.

Texas Instruments, Digital Micromirror Device, http://www.ti.com/dlp/docs/papers/state/state.htm.

* cited by examiner

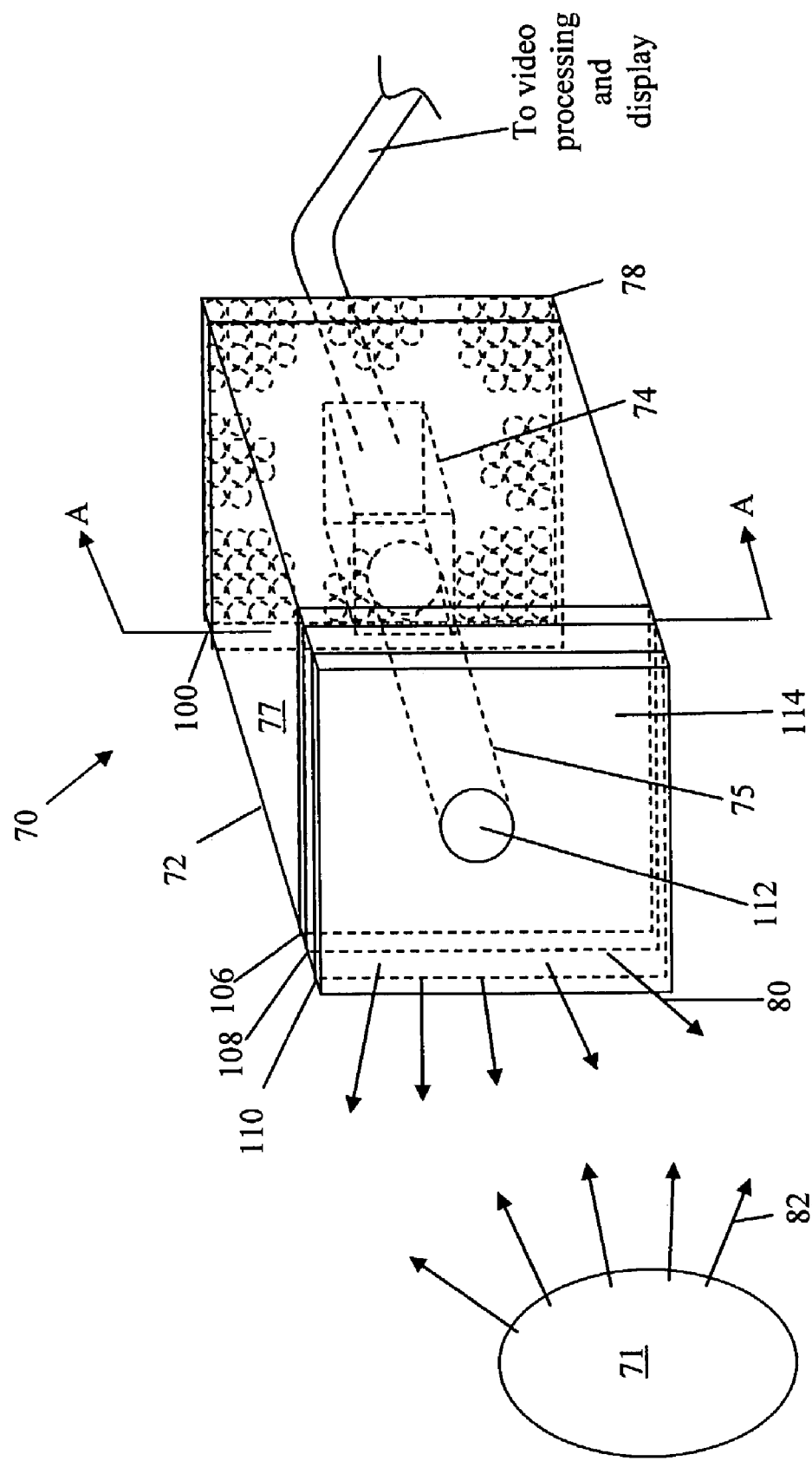

IMAGING SYSTEM USING DIFFUSE INFRARED LIGHT

RELATED APPLICATIONS

This application is a continuation-in-part, and claims priority benefit, of U.S. patent application Ser. No. 09/487,007 filed Jan. 19, 2000, entitled Diffuse Infrared Light Imaging System, which issued as U.S. Pat. No. 6,556,858 on Apr. 29, 2003 (hereby specifically incorporated by reference in its entirety).

TECHNICAL FIELD

The present invention is generally directed to generation of diffuse infrared light. More particularly, the invention is directed to a system for illuminating an object with diffuse infrared light and producing a video image of the object based on reflected infrared light.

BACKGROUND OF THE INVENTION

Some medical procedures and treatments require a medical practitioner to locate a blood vessel in a patient's arm or other appendage. This can be a difficult task, especially when the blood vessel lies under a significant deposit of subcutaneous fat. The performance of previous imaging systems designed to aid in finding such blood vessels has been lacking.

Therefore, a system for enhancing the visual contrast between subcutaneous blood vessels and surrounding tissue is needed.

SUMMARY OF THE INVENTION

The foregoing and other needs are met by an apparatus for providing diffuse light towards an object, such as a patient, to enhance visibility of subcutaneous blood vessels. In one embodiment, the apparatus includes an array of light-emitting sources. Each light-emitting source is operable to emit infrared light having a wavelength toward the object. A power source provides power to the array, and the array can emit infrared light when the power source is enabled. The apparatus further includes a diffusing structure having more than one diffusion stage. Each diffusion stage provides a level of diffusion to the infrared light emitted from the array as the emitted light passes through the diffusing structure.

In another embodiment, an apparatus is disclosed for providing diffuse light to an object. The apparatus includes an array of light-emitting sources, each source for emitting infrared light having a wavelength toward the object. A power source provides power to the array. The apparatus further includes diffusing structure which provides various levels of diffusion to the infrared light emitted from the array. The diffusing structure includes a first diffusing layer which is disposed adjacent to the array. The first diffusion layer provides a first level of diffusion to the light emitted by the array. A second diffusing layer is spaced apart from the first diffusing layer and provides a second level of diffusion to the light emitted by the array. A polarizer is included to polarize the light emitted by the array.

In yet another embodiment, an apparatus is disclosed which provides diffuse light to an object. The apparatus includes a light source for emitting infrared light toward the object. A first diffusing layer having a first diffusing plane intercepts light from the light source and provides a first amount of diffusion to the infrared light emitted by the light source. The apparatus includes a video imaging device for receiving light reflected from the object. The video imaging device operates to provide a video image of the object based on the reflected light.

In yet another embodiment, an apparatus is disclosed for providing diffuse light to an object. Groups of light-emitting diodes (LEDs) are arranged in a select pattern which define an LED plane. Each LED has an emitting surface for emitting infrared light towards the object and an electrical input for providing an electrical signal to the LED. The apparatus includes a control circuit which provides control signals to activate one or more LEDs in a select group of LEDs. A diffusing structure is positioned to intercept and diffuse the infrared light emitted from one or more of the LEDs.

Using the invention described herein, subcutaneous blood vessels that are difficult or impossible to see under white light or under non-diffuse infrared light can be easily seen in a video image, where the subcutaneous blood vessels appear as dark lines against a lighter background of surrounding flesh.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIG. 6b is a cross-sectional view of the imaging system of FIG. 6a;

FIG. 7b is a cross-sectional view of the imaging system of FIG. 7a;

FIG. 8 is an isometric view of yet another aspect of an imaging system;

DETAILED DESCRIPTION OF THE PREFERRED EMBODIMENT

Skin and some other body tissues reflect infrared light in the near-infrared range of about 700 to 900 nanometers, while blood absorbs radiation in this range. Thus, in video images of body tissue taken under infrared illumination, blood vessels appear as dark lines against a lighter background of surrounding flesh. However, due to the reflective nature of subcutaneous fat, blood vessels that are disposed below significant deposits of such fat can be difficult or impossible to see when illuminated by direct light, that is, light that arrives generally from a single direction.

The inventor has determined that when an area of body tissue having a significant deposit of subcutaneous fat is imaged in near-infrared range under illumination of highly diffuse infrared light, there is significantly higher contrast between the blood vessels and surrounding flesh than when the tissue is viewed under direct infrared illumination. Although the invention should not be limited by any particular theory of operation, it appears that most of the diffuse infrared light reflected by the subcutaneous fat is directed away from the viewing direction. Thus, when highly diffuse infrared light is used to illuminate the tissue, the desired visual contrast between the blood vessels and the surrounding flesh is maintained.

Figure 1:
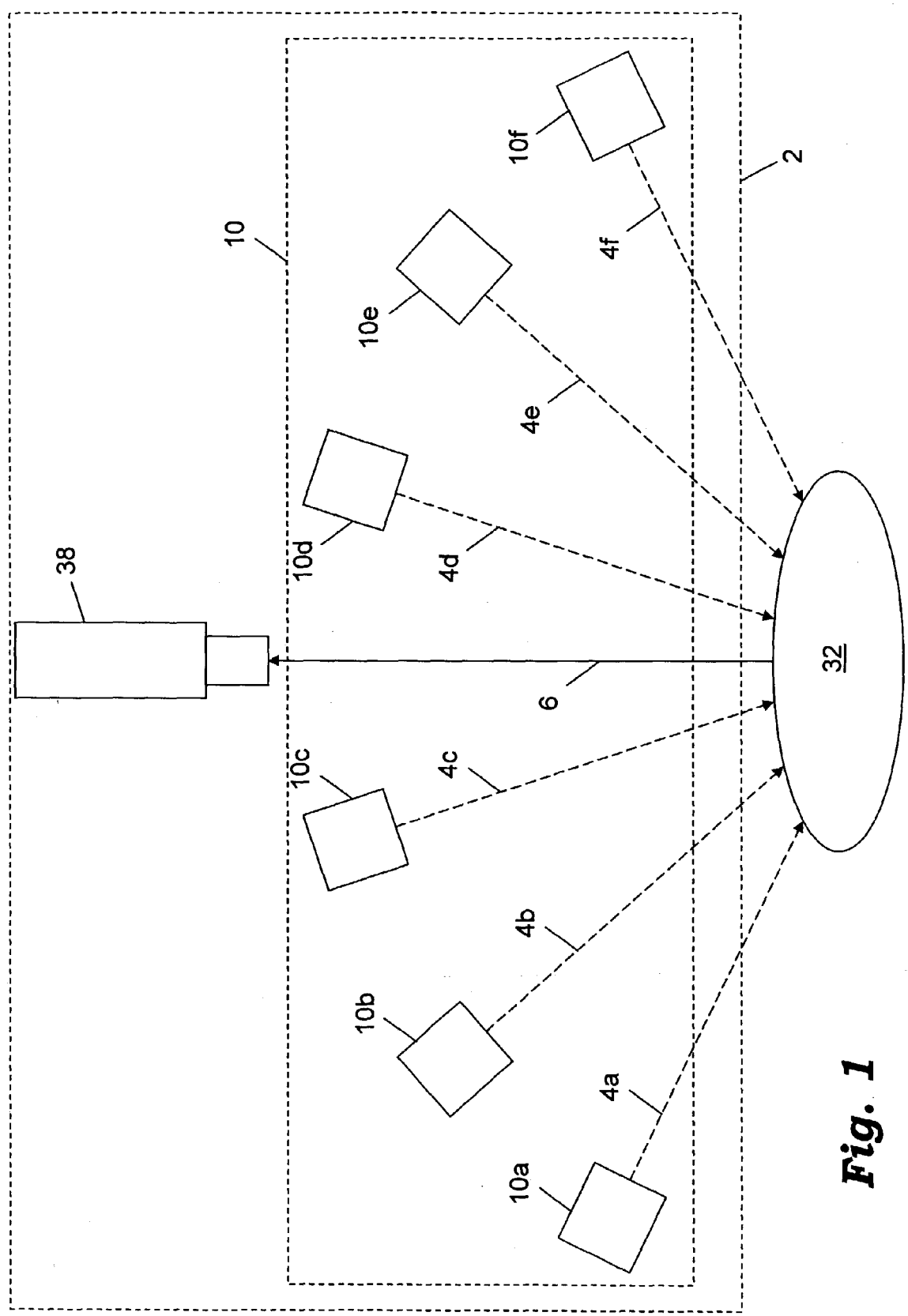
FIG. 1 depicts an imaging system for viewing an object under infrared illumination according to a preferred embodiment of the invention.

Shown in FIG. 1 is an imaging system 2 for illuminating an object 32, such as body tissue, with highly diffuse infrared light, and for producing a video image of the object 32 based upon infrared light reflected from the object 32. As described in detail herein, when the object 32 is body tissue, blood vessels that are disposed below subcutaneous fat in the tissue may be clearly seen in a video image produced by the system 2.

The imaging system 2 includes an illumination system 10 that illuminates the object 32 with infrared light from multiple different illumination directions. The system 10 includes multiple infrared light providers 10a-10f, each providing infrared light to the object 32 from a different illumination direction. The directions of arrival of the infrared light from each light provider 10a-10f are represented in FIG. 1 by the rays 4a-4f. As shown in FIG. 1, the directions of arrival of the infrared light ranges from perpendicular or near perpendicular to the surface of the object 32, to parallel or near parallel to the surface of the object 32. Since the infrared illumination arrives at the object 32 from such a wide range of illumination directions, the infrared illumination is highly diffuse.

As described in greater detail hereinafter, the light providers 10a-10f are preferably light reflecting surfaces that direct light from a single light source toward the object 32. In other embodiments, the light providers 10a-10f are individual light sources, or combinations of light sources and reflectors.

The imaging system 2 also includes an imaging device 38, such as a video camera, for viewing the object 32. The imaging device 38 views the object 32 from a viewing direction which is represented in FIG. 1 by the arrow 6. The imaging device 38 receives the diffuse infrared light reflected from the object 32, and generates an electronic video image of the object 32 based on the reflected infrared light.

Figure 2:
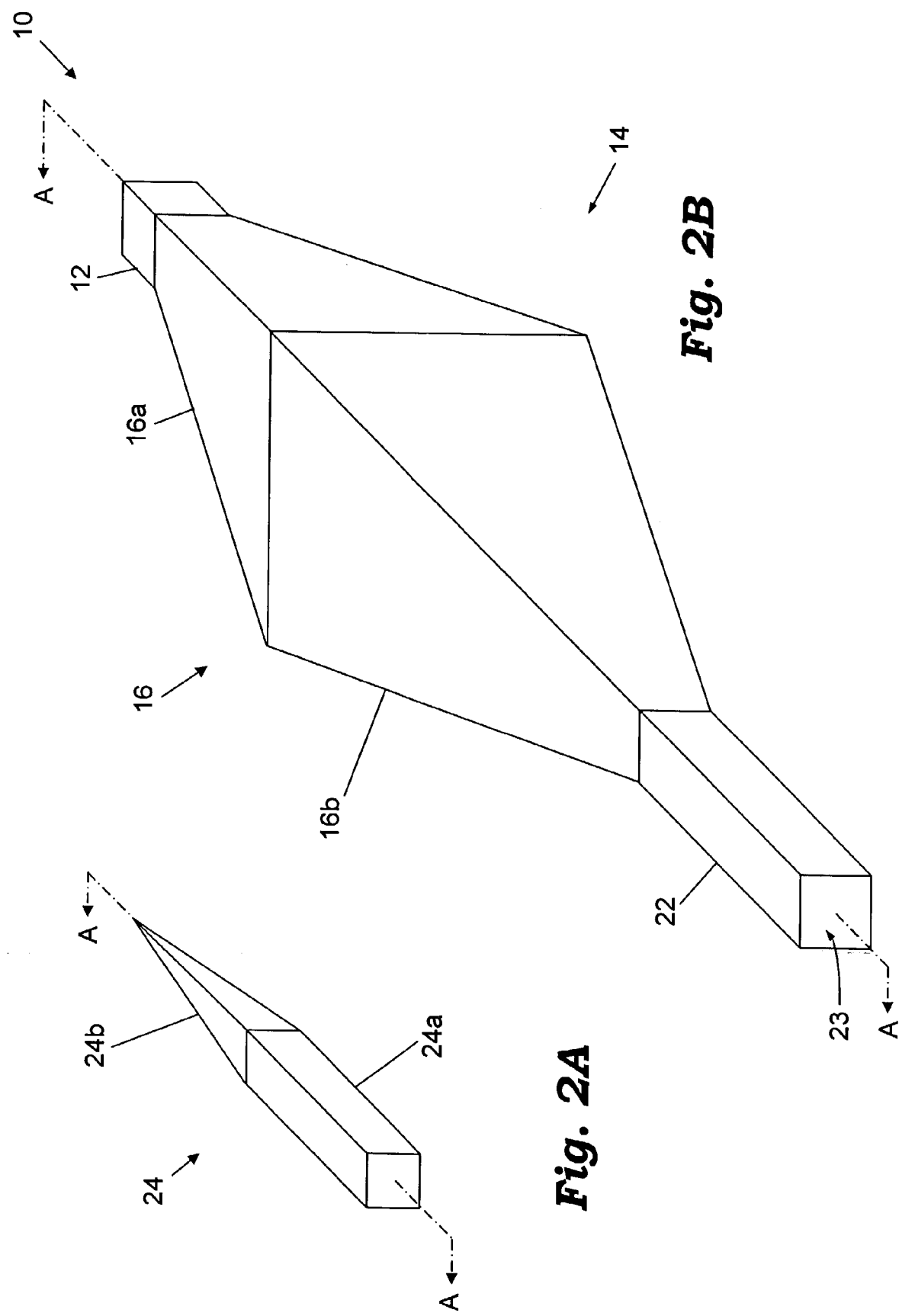
FIGS. 2a and 2b are perspective views of an imaging system using diffuse infrared light according to a preferred embodiment of the invention.
Figure 3:
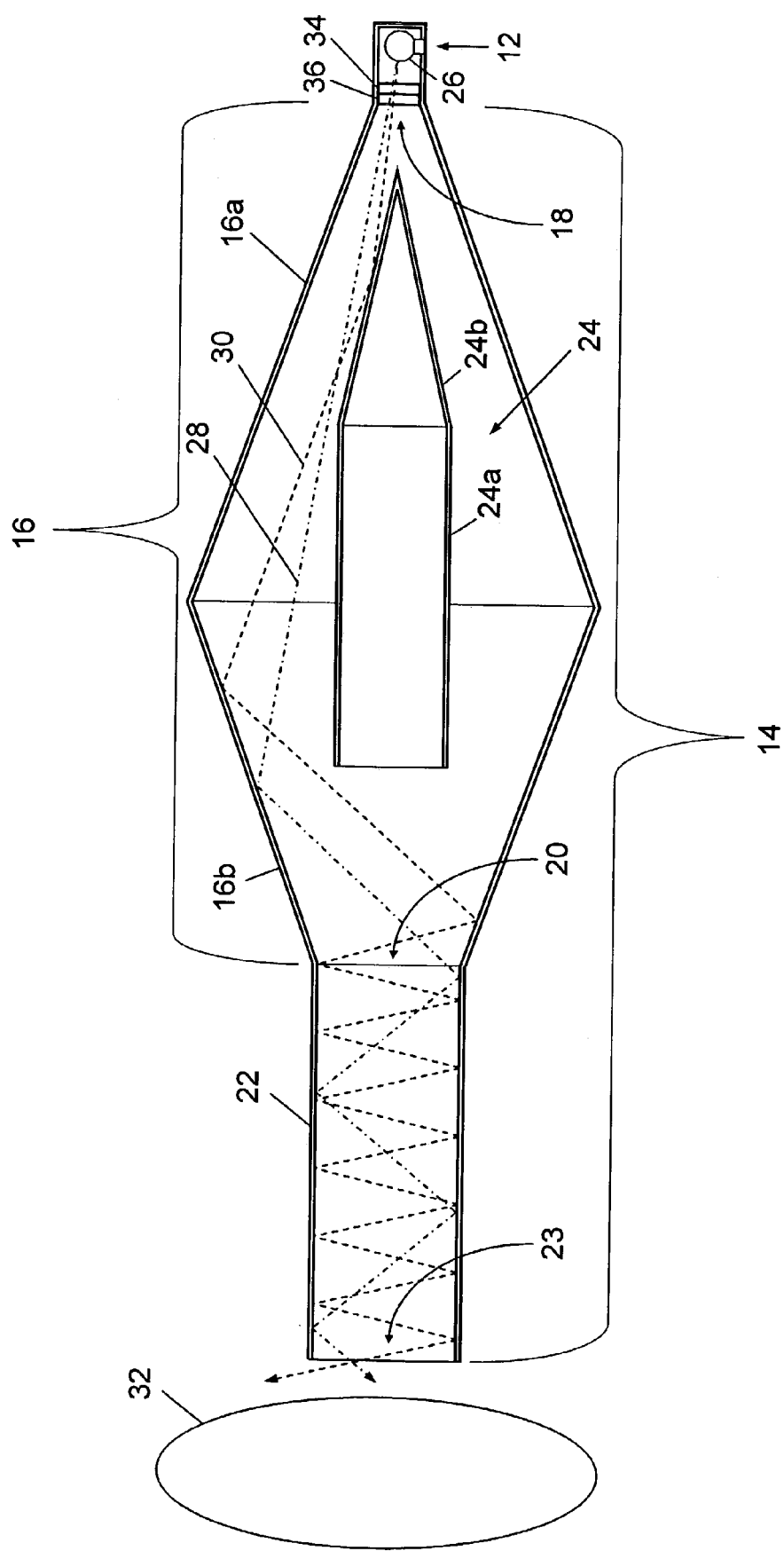
FIGS. 3 and 4 are cross-sectional views of the imaging system according to a preferred embodiment of the invention.

Shown in FIGS. 2a and 2b is a preferred embodiment of the illumination system 10. FIG. 3 depicts a cross-sectional view of the system 10 corresponding to the section A-A as shown in FIGS. 2a-b. The system 10 preferably includes a light source 12 that emits light into one end of a light diffusing structure 14. The light diffusing structure 14 includes an elongate outer enclosure 16 having reflective inner surfaces. Preferably, the inner surfaces of the elongate outer enclosure 16 are white in color. Alternatively, these reflective surfaces are mirrored surfaces, or a combination of white and mirrored surfaces. At the end of the light diffusing structure 14 opposite the light source 12, is a hollow light guide 22. As described in more detail below, the light guide 22 serves as an output aperture for the diffuse light.

The elongate outer enclosure 16 includes first and second sections 16a and 16b, each having a large end and a small end. Preferably, the first and second sections 16a and 16b are substantially pyramidal in shape, each having four trapezoidal faces. In the preferred embodiment, the four trapezoidal faces of the sections 16a and 16b are identical, such that each end of the sections 16a and 16b forms a square aperture. As shown in FIGS. 2a and 2b, the larger ends of the first and second sections 16a and 16b are joined together to form the enclosure 16.

At the small end of the first section 16a is an input aperture 18 formed by the four short sides of the four trapezoidal faces of the section 16a. The light source 12 is preferably attached to the small end of the first section 16a at the input aperture 18. Thus, the light generated by the light source 12 enters the elongate enclosure 16 at the input aperture 18, and illuminates the interior surfaces of the enclosure 16.

At the small end of the second section 16b is an output aperture 20 formed by the four short sides of the four trapezoidal faces of the section 16b. Attached at the output aperture 20 is one end of the hollow light guide 22. The light guide 22 preferably has white reflective inner surfaces similar to the inner surfaces of the enclosure 16.

The system 10 also includes an elongate inner reflector 24 which is disposed within and preferably coaxial with the outer enclosure 16. For clarity, the inner reflector 24 is shown in FIG. 2b removed from the outer enclosure 16. In the preferred embodiment, the inner reflector 24 is formed from a square tubular section 24a joined to the square base of a pyramidal section 24b. Preferably, the pyramidal section 24b has four sides that taper down to an apex. As shown in FIG. 3, the apex of the pyramidal section 24b is disposed proximate the input aperture 18 of the outer enclosure 16. The inner reflector 24 has reflective white outer surfaces similar to those of the inner surfaces of the outer enclosure 16.

The light diffusing characteristics of the structure 14 are best understood with reference to FIG. 3. Within the light source 12 is a lamp 26, such as a quartz-halogen bulb and gold-plated reflector manufactured by Gilway and having part number L517A-G. When energized, the lamp 26 produces electromagnetic radiation in the form of white light.

For purposes of this description, the lamp 26 may be thought of as a point source radiating light in multiple directions, as represented by the exemplary rays 28 and 30. As shown in FIG. 3, the ray 28 reflects from the inner surface of the section 16b of the outer enclosure 16. The ray 28 then travels through the output aperture 20, into the light guide 22, and, after multiple reflections from the inner surfaces of the light guide 22, emits from the exit aperture 23. The ray 30, which exits the light source 12 from a different angle than the ray 28, reflects from the inner reflector 24. The ray 30 then reflects from the inner surface of the section 16b of the outer enclosure 16, and travels through the output aperture 20 and into the light guide 22. After multiple reflections from the inner surfaces of the light guide 22, the ray 30 also emits from the exit aperture 23, but at a different angle than that of the ray 28.

When an object 32 is placed near the exit aperture 23, the rays 28 and 30 arrive at the object 32 from different angles. It will be appreciated that the light radiating from the light source 12 could be represented as an infinite number of rays which strike and reflect from the inner reflector 24 and the inner surfaces of the outer enclosure 16 from an infinite number of angles. Thus, the light emitted from the exit aperture 23 arrives at the object 32 from many different angles, and is therefore highly diffuse light. These arrival angles range from near perpendicular to near parallel with the plane of the exit aperture 23. Since the diffusing structure 14 is three-dimensional, it will be appreciated that light also reflects from the other surfaces of the outer enclosure 16 and the inner reflector 24, such as those that are perpendicular to the surfaces shown in FIG. 3. Therefore, the light emitted at the exit aperture 23 of the illumination system 10 is highly diffuse, appearing to be generated by many different light sources.

Due to the arrangement of the reflective inner surfaces of the outer enclosure 16 and the reflective outer surfaces of the inner reflector 24, the diffusing structure 14 efficiently transfers the light radiated from the lamp 26 to the exit aperture 23. Thus, a very large fraction of the light provided by the lamp 26 reaches the object 32, and very little light energy is wasted.

As described in more detail below, the illumination system 10 can be used to provide diffuse light for medical imaging purposes. However, it will be appreciated that the scope of the invention is not limited to medical uses. The system 10 could also be used as a diffuse light source for general photographic purposes.

In a preferred embodiment of the invention, as depicted in FIG. 3, the light source 12 includes a cold mirror 34 disposed between the lamp 26 and the input aperture 18 of the outer enclosure 16. The cold mirror 34 reflects substantially all light having wavelengths outside a selected infrared range of wavelengths. Preferably, the selected range includes wavelengths from approximately 700 to 1000 nanometers. Immediately proximate the cold mirror 34, and disposed between the cold mirror 34 and the input aperture 18, is an infrared transmitting filter 36 which further attenuates light having wavelengths outside the selected infrared range while transmitting light having wavelengths within the selected infrared range. Thus, the light that passes through the cold mirror 34 and the filter 36 into the outer enclosure 16 is infrared light having wavelengths within the selected infrared range.

It should be appreciated that there are other ways that the light source 12 could be configured to generate infrared light. For example, the light source 12 could consist of an infrared light-emitting diode (LED) or an array of infrared LED's. Thus, the configuration of the light source 12 shown in FIG. 3 and described above is a preferred embodiment only, and the invention is not limited to any particular configuration of the light source 12.

Figure 4:
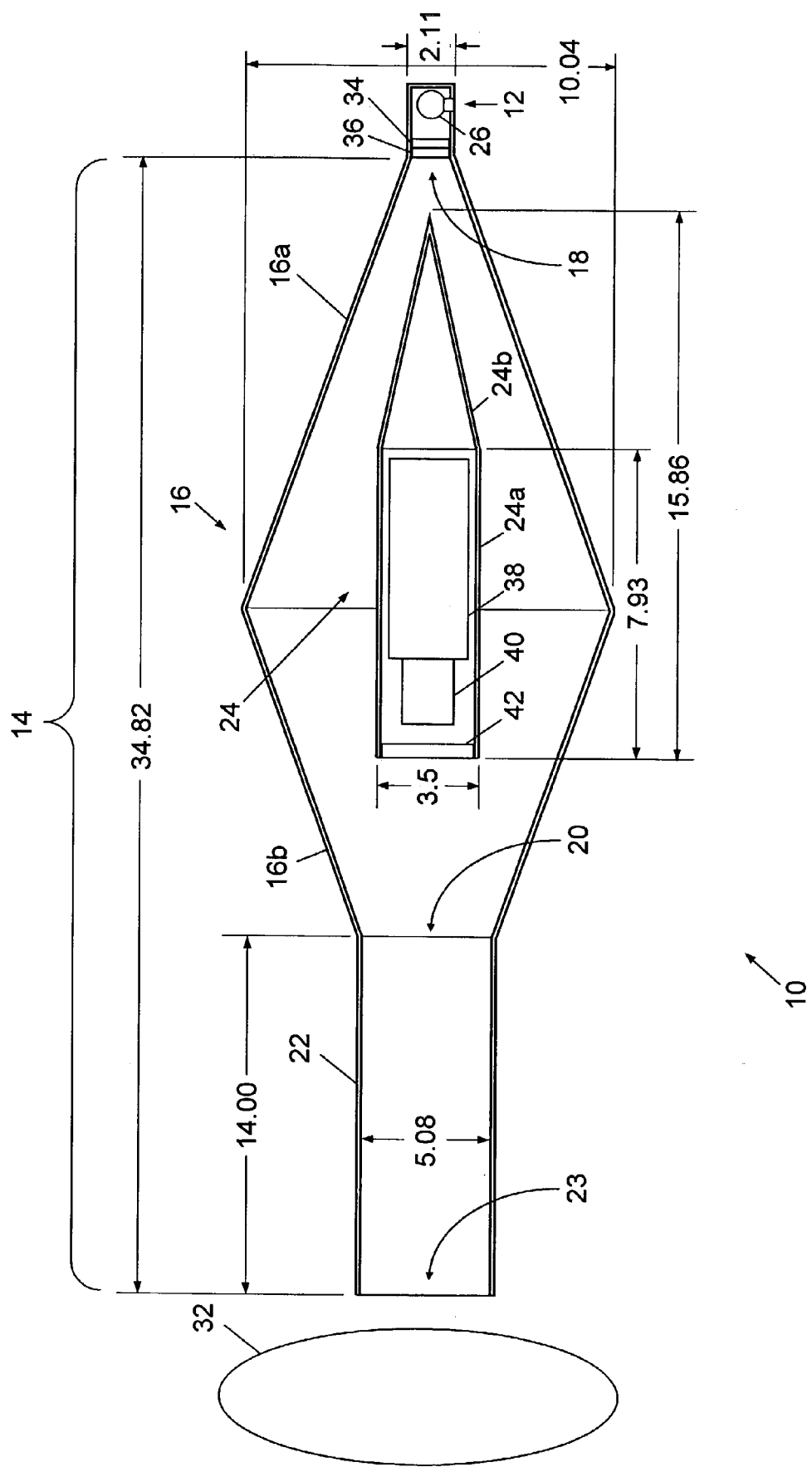

FIG. 4 depicts the dimensions of a preferred embodiment of the illumination system 10. As shown in FIG. 4, the total length of the light diffusing structure 14 is approximately 34.82 inches. The height and width of the outer enclosure 16 at the juncture of the first and second sections 16a and 16b is approximately 10.04 inches. The preferred length of the light guide 22 is approximately 14.00 inches, and its height and width is approximately 5.08 inches. Preferably, the total length of the inner reflector 24 is approximately 15.86 inches. The preferred length of the tubular section 24a of the inner reflector 24 is approximately 7.93 inches. The height and width of the tubular section 24a is approximately 3.5 inches. The height and width of the light source 12 is approximately 2.11 inches.

As shown in FIG. 4, a preferred embodiment of the invention includes a lens 40 used in conjunction with the video imaging device 38 to produce a video image of the object 32 based on diffuse light reflected from the object 32. Preferably, the imaging device 38 of this embodiment is a charge-coupled device (CCD) video camera 38 manufactured by Cohu, having model number 631520010000. The lens 40 of the preferred embodiment is a 25 mm f-0.95 movie camera lens manufactured by Angenieux.

The camera 38 and lens 40 of the preferred embodiment are disposed within the tubular section 24a of the inner reflector 24. As shown in FIG. 4, the open end of the tubular section 24a forms an aperture toward which the camera 38 and lens 40 are pointed. In this manner, the hollow light guide 22 is substantially centered within the field of view of the camera 38. Thus, the camera 38 receives light reflected from the object 32 that enters the light guide 22, travels through the enclosure 16, and enters the open end of the section 24a.

As shown in FIG. 4, the preferred embodiment of the invention includes an infrared-transmitting filter 42 disposed in the open end of the tubular section 24a. This filter 42 receives light reflected from the object 32, and any other light that may enter the enclosure 16, and substantially eliminates all light having wavelengths outside the infrared range of approximately 700 to 1000 nanometers. In the preferred embodiment, the filter 42 substantially eliminates light having wavelengths outside a selected infrared range of approximately 800 to 850 nanometers. Thus, the light that passes through the filter 42 and into the lens 40 is infrared light within the selected wavelength range. Therefore, the camera 38 primarily receives infrared light which originates from within the illumination system 10 and which is reflected from the object 32.

Figure 5:
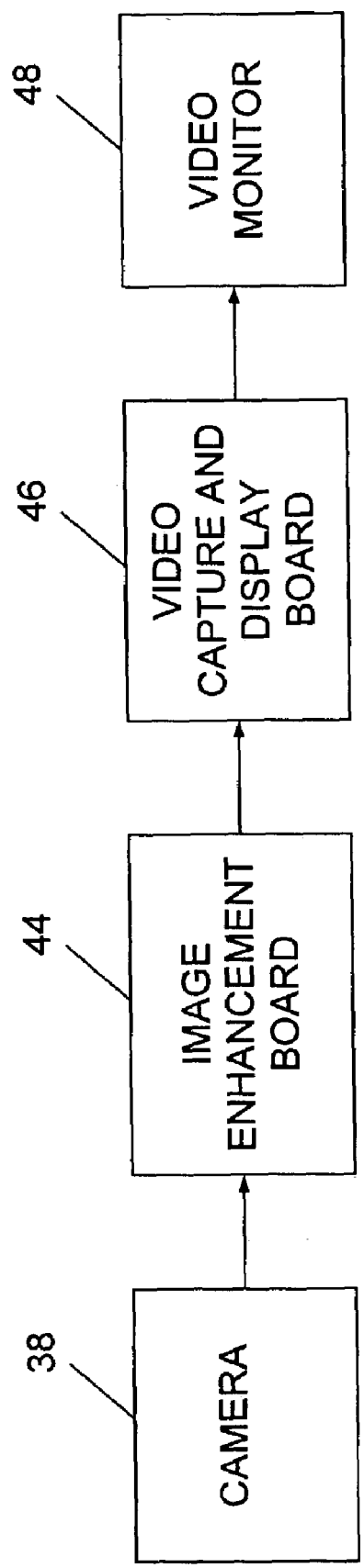
FIG. 5 is a functional block diagram of the imaging system according to a preferred embodiment of the invention.

Based on the light reflected from the object 32, the camera 38 generates a video image of the object 32 in the form of an electrical video signal. As shown in FIG. 5, the video signal is preferably provided to an image enhancement board 44, such as a board manufactured by DigiVision having a model number ICE-3000. The board 44 generates an enhanced video image signal based on the video signal from the camera 38. The enhanced video image signal is provided to a video capture and display card 46, such as a model 20-TD Live card manufactured by Miro. The card 46 captures still images from the image signal which may be saved in digital format on a digital storage device. The card 46 also formats the video image signal for real-time display on a video monitor 48.

It should be appreciated that the illumination system 10 could use other means for generating diffuse infrared light in accordance with the invention. For example, the light providers 10a-10f of FIG. 1 could be embodied by a ring-light strobe light. Alternatively, a circular array of LED's could be used to illuminate a plastic transmitting diff-user placed near the surface of the object 32. In the latter embodiment, the light providers 10a-10f would correspond to the individual LED's in the array.

Figure 6A:
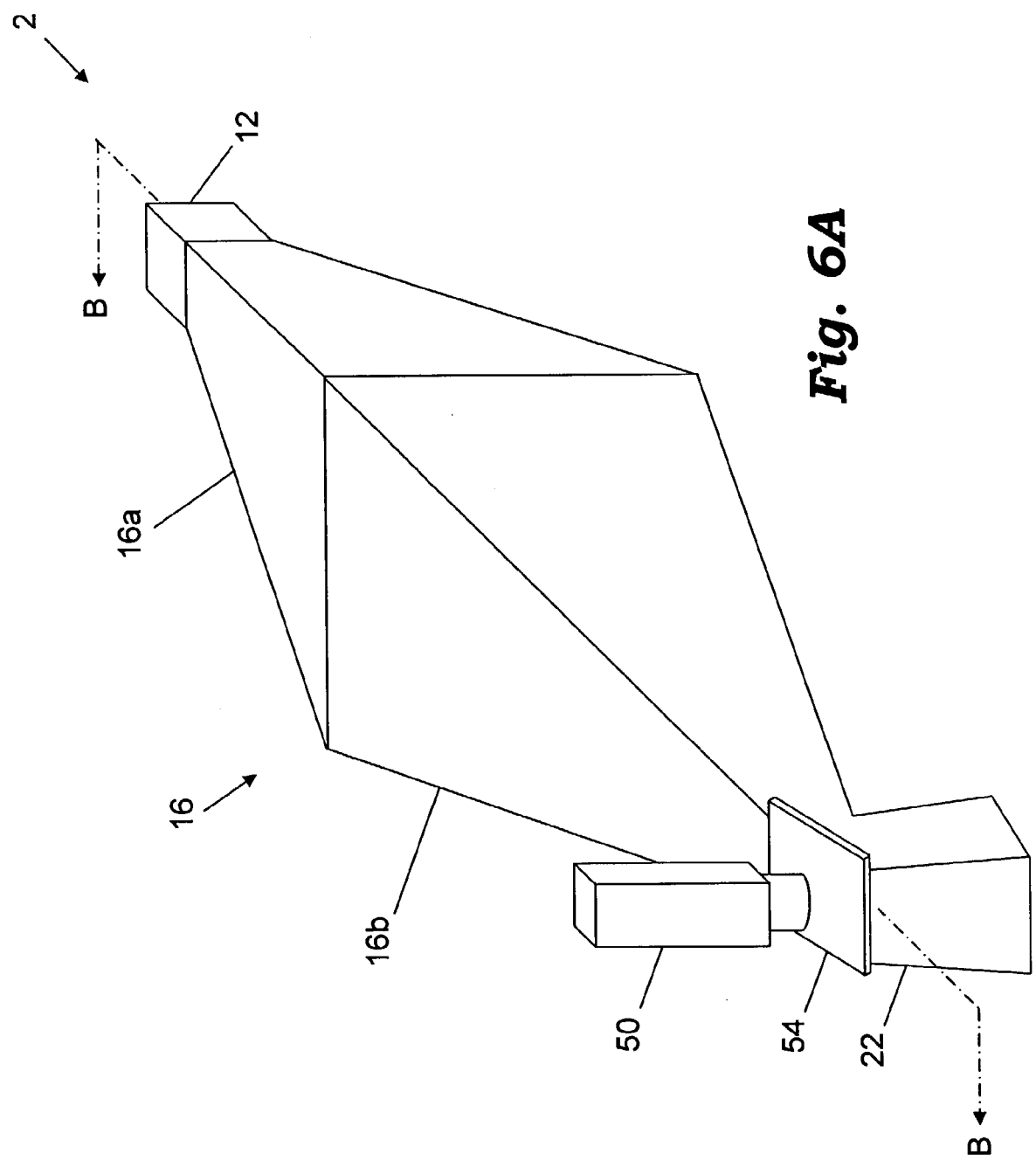
FIG. 6a is a perspective view of an imaging system using diffuse infrared light according to an alternative embodiment of the invention.
Figure 6B:
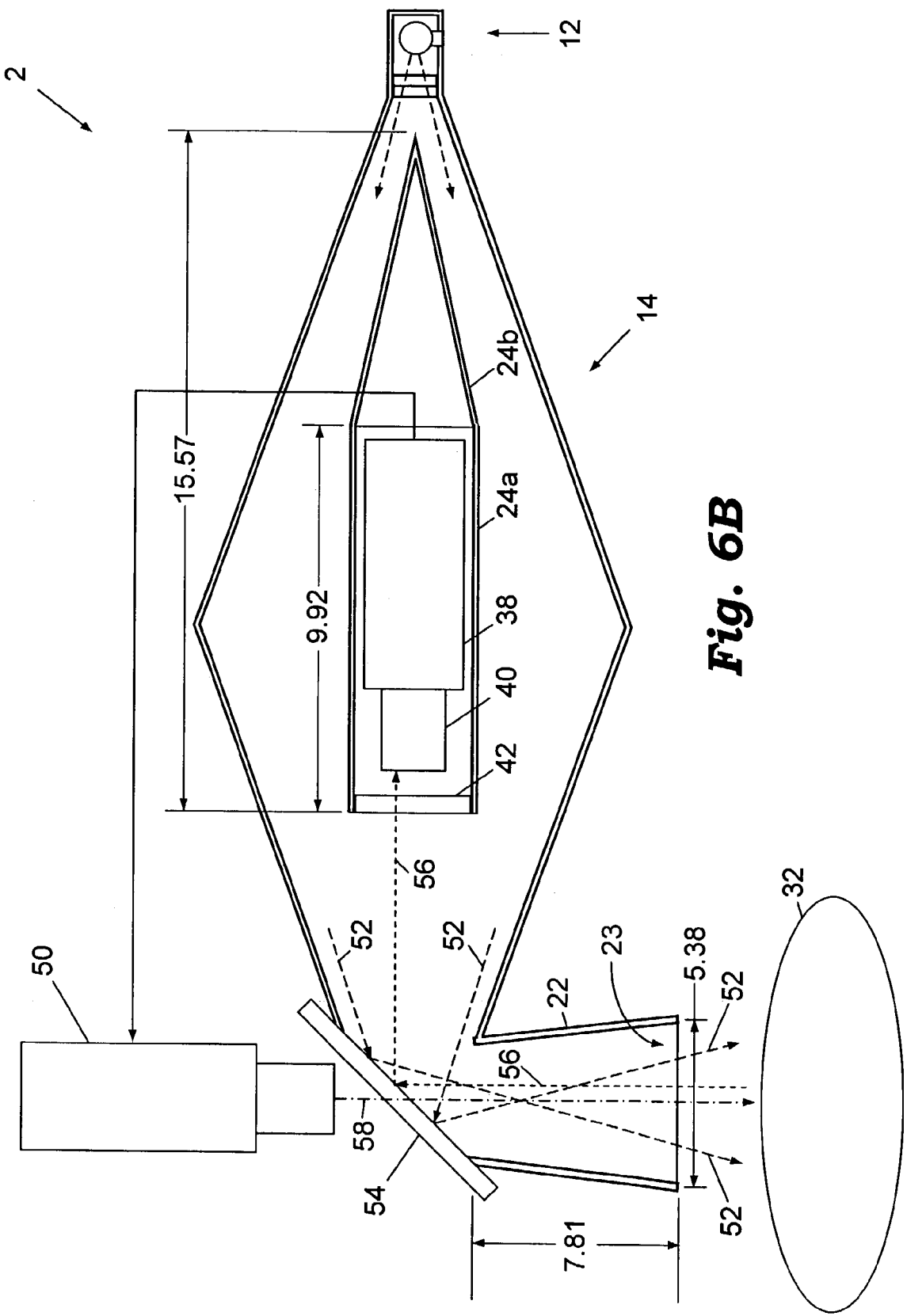

In an alternative embodiment of the invention depicted in FIGS. 6a and 6b, the imaging system 2 includes a video projector 50 for illuminating the object 32 with an image of the object 32 to enhance the visual contrast between lighter and darker areas of the object 32. As described in U.S. Pat. No. 5,969,754, entitled CONTRAST ENHANCING ILLUMINATOR, the contents of which are incorporated herein by reference, the features of an object are visually enhanced for an observer when the features of a projected visible-light image of the object overlay the corresponding features of the object. The overlaid visible-light image causes the bright features of the object to appear brighter while the dark areas remain the same.

The embodiment of the invention shown in FIGS. 6a and 6b provides diffuse infrared light (represented by the rays 52) to the object 32 in a manner similar to that described previously. However, in the embodiment shown in FIGS. 6a and 6b, the optical path of the illuminating light is folded, such that the exit aperture 23 of the light guide 22 is rotated by 90 degrees relative to the exit aperture shown in FIGS. 1-3.

As shown in FIG. 6b, a beam separator, such as a hot mirror 54, receives infrared light 52 from the interior of the light diffusing structure 14 and reflects the infrared light 52 into the light guide 22 and toward the object 32. The hot mirror 54 also receives an infrared image of the object 32 (represented by the ray 56) and reflects it toward the camera 38. The hot mirror 54 receives the visible-light image (represented by the ray 58) from the projector 50 and transmits it into the light guide 22 and toward the object 32.

As explained in greater detail in U.S. Pat. No. 5,969,754, the video output signal from the video camera 38 is provided as a video input signal to the projector 50. Based on the video input signal, the projector 50 projects the visible-light image 58 of the object 32 toward the hot mirror 54. The hot mirror 54 receives the visible-light image 58 and transmits it into the light guide 22 toward the object 32. By proper alignment of the projected visible-light image 58 from the projector 50 with the infrared image 56 of the object 32 which is sensed by the camera 38, the features in the projected visible-light image 58 are made to overlay the corresponding features of the object 32.

When the object 32 is body tissue, and the invention is used to find subcutaneous blood vessels in the body tissue, the blood vessels appear as dark lines in the projected visible-light image 58. Thus, when the visible-light image 58 is projected onto the body tissue, the subcutaneous blood vessels will lie directly beneath the dark lines in the projected visible-light image 58. In this manner, the invention significantly improves a medical practitioner's ability to find subcutaneous blood vessels while minimizing discomfort for the patient.

Figure 7A:
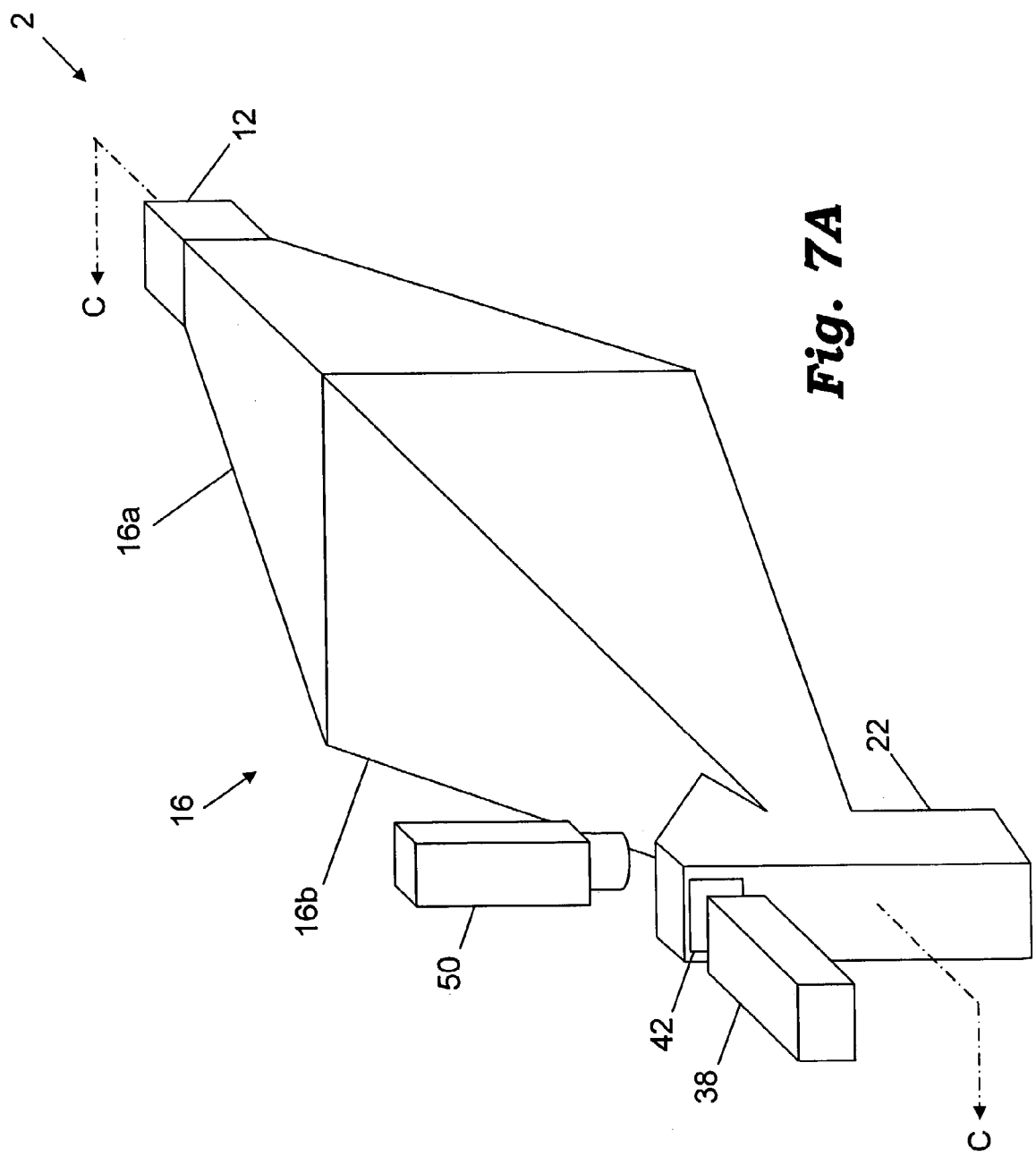
FIG. 7a is a perspective view of an imaging system using diffuse infrared light according to another embodiment of the invention.
Figure 7B:
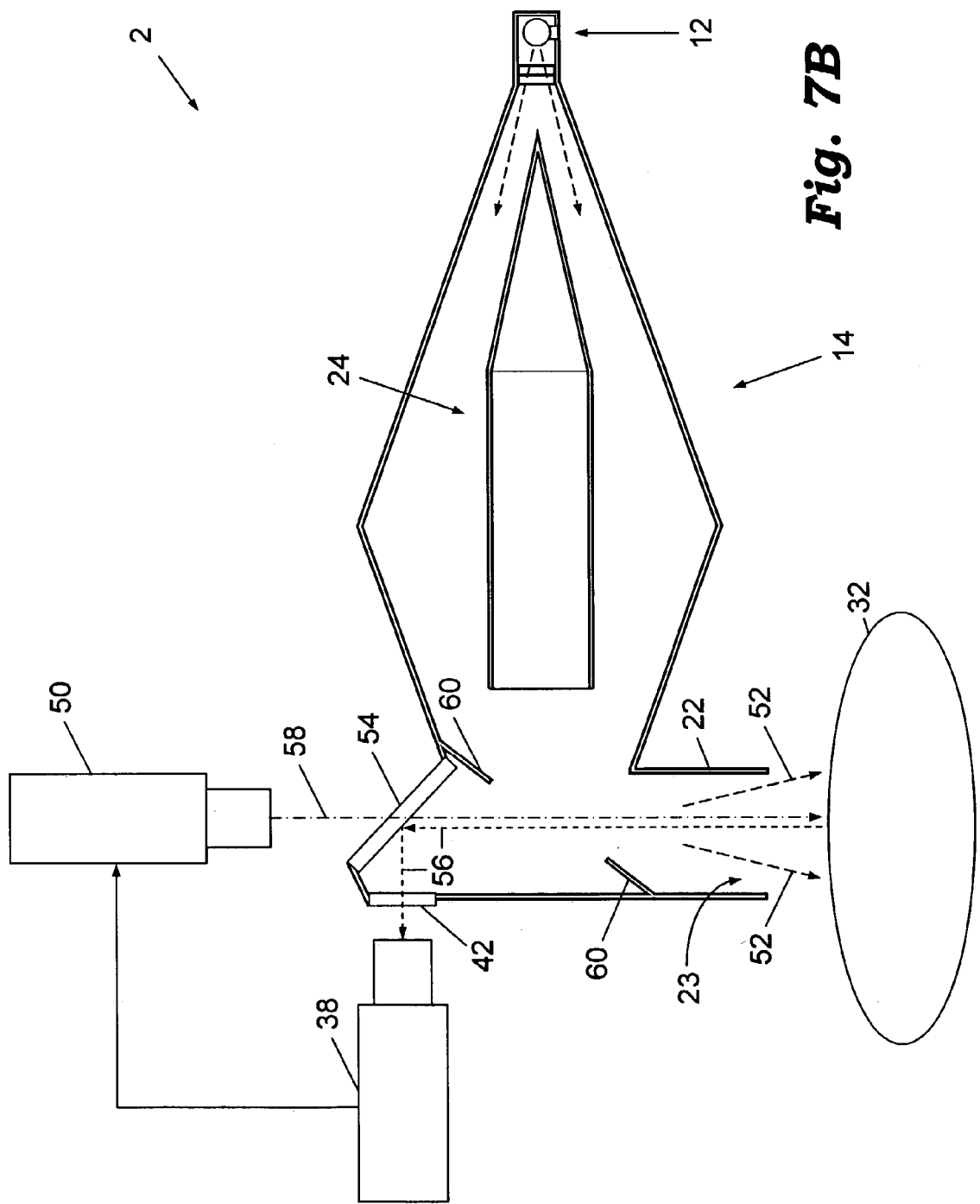

FIGS. 7a and 7b depict an alternative embodiment of the invention for use as a contrast enhancing illuminator. The embodiment of FIGS. 7a-b operates in a fashion similar to the embodiment of FIGS. 6a and 6b. However, in the embodiment of FIGS. 7a-b, the camera 38 is located outside the light diffusing structure 14. To accommodate the different location of the camera 38, the hot mirror 54 shown in FIGS. 7a-b is rotated by 90 degrees clockwise relative to its position in FIGS. 6a-b. Otherwise, the hot mirror 54 serves a similar function as that described above in reference to FIGS. 6a-b. Also to accommodate the different camera location, the infrared-transmitting filter 42 is mounted in a wall of the light guide 22. A reflective panel 60 is provided in this embodiment to further direct the light from the light source 12 into the light guide 22 and toward the exit aperture 23. Preferably, the panel 60 is a flat reflective sheet having an orifice therein to allow light to pass between the object 32 and the camera 38 and projector 50.

A preferred embodiment of a relatively compact and highly reliable imaging system 70 is depicted in FIGS. 8-11. The imaging system 70 is most preferably configured to illuminate an object 71, such as body tissue and the like, and to produce a video image of the object 71 based upon infrared light reflected from the object 71. The imaging system 70 preferably includes a housing 72 which contains the imaging features of the system 70.

As shown in FIG. 8, the housing 72 preferably has a substantially rectangular configuration. The housing 72 preferably has a length of between about three and about five inches and a width of about three and one-half inches. It will be appreciated by those skilled in the art that the imaging system 70 can be configured in a variety of ways and the invention should not be limited by any specific examples or embodiments discussed herein. For example, in FIG. 8 the housing is depicted as being substantially rectangular, however, circular, polygonal, and other geometries and sizes are feasible as well.

Figure 9:
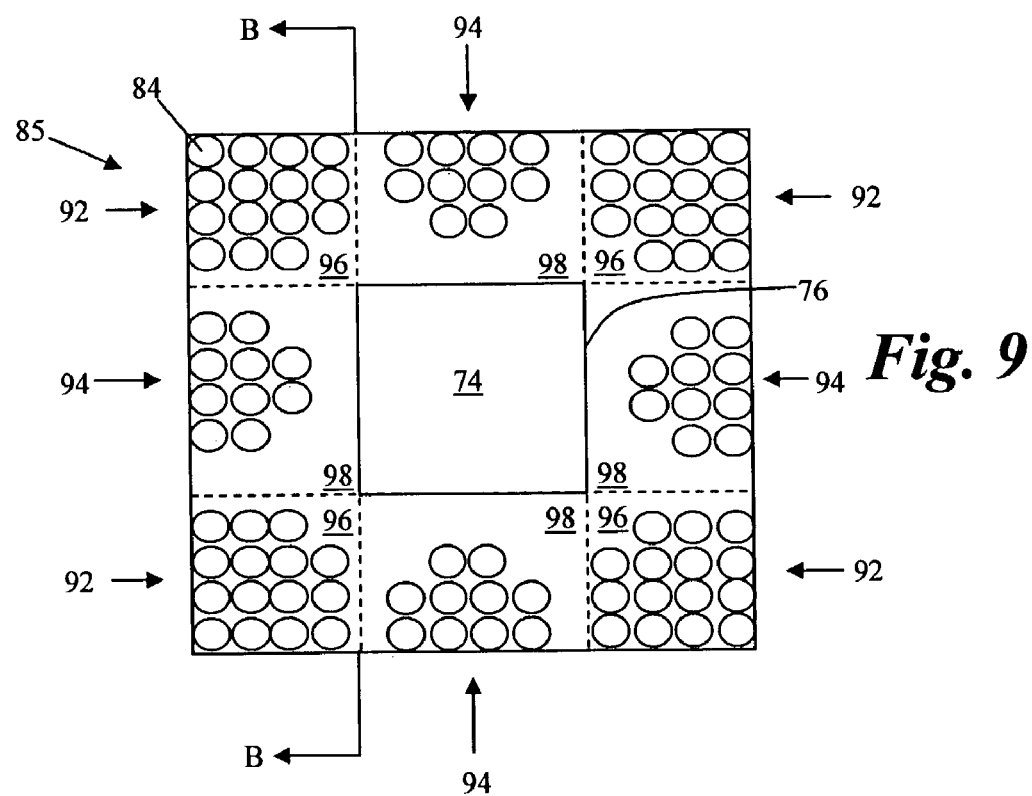
FIG. 9 is a front view of a portion of the imaging system as viewed in the direction of the arrows taken along line A-A of FIG. 8.

An imaging device 74, such as a video camera having a lens 75, and video processing components reside within the housing 72. The imaging device 74 and video processing components operate to detect infrared light and to process the detected infrared light from the object 71. The imaging system 74 produces an image based on the detected infrared light reflected from the object 71, as described herein. As shown in FIGS. 8 and 9, the imaging device 74 is preferably mounted within an aperture 76 of mounting wall 78, with the lens 75 extending into the housing interior 77, as described further below. More particularly, the camera 74 is preferably centrally and symmetrically mounted within the housing 72. This preferred symmetrical camera location tends to maximize the amount of light detected by the camera, which enhances the image produced by the system 70, thereby enhancing the illumination of blood vessels disposed below subcutaneous fat in body tissue.

The housing 72 most preferably contains various components operable to transmit diffuse light from the system 70 toward the object 71. Arrows 80 represent diffuse light transmitted by the system 70. Arrows 82 represent the light reflected from the object 71. As shown in FIG. 9, as viewed in the direction of the arrows along the section line A-A of FIG. 8, the wall 78 contains a number of infrared light emitting diodes (LEDs) 84 disposed in a LED array 85 for emitting infrared light. The LED array 85 defines a LED plane of reference. When activated, each LED 84 preferably transmits light at a wavelength of about 740 nanometers (nm). In the preferred embodiment, each LED 84 is manufactured by Roithner Lasertechnik of Austria under model number ELD-740-524.

Figure 10:
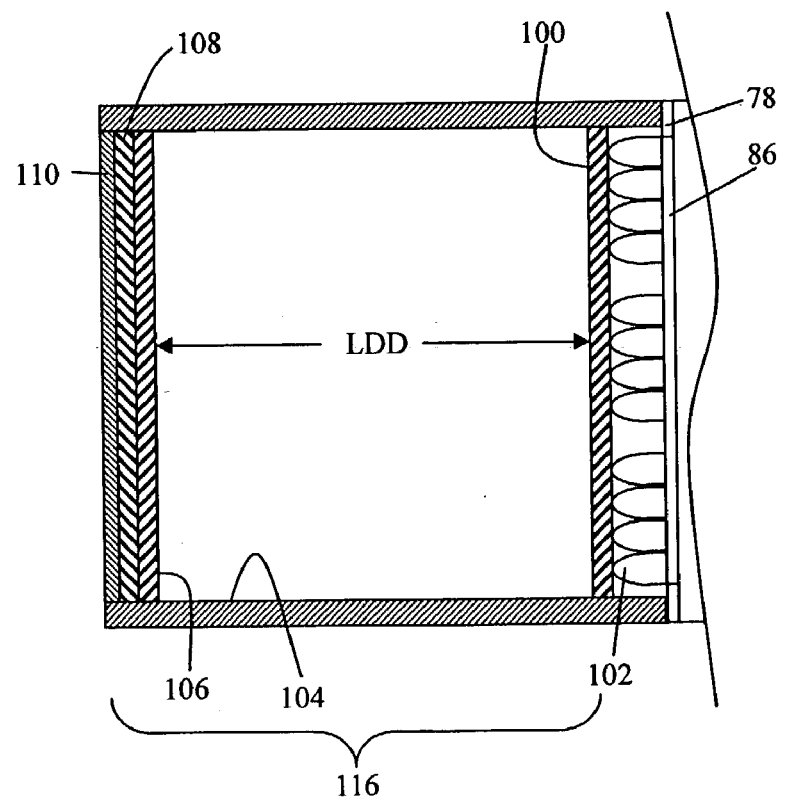
FIG. 10 is a cross-sectional side view taken along line B-B of FIG. 9.

As shown in FIG. 10, and according to the preferred embodiment, the LEDs 84 are mounted on a circuit board 86 located adjacent to wall 78. As shown in FIG. 9, there are most preferably eight groups 92, 94 of LEDs 84 concentrically arranged about the imaging system 74. The concentric LED arrangement tends to provide maximal dispersion and transmission of diffuse light from the system 70. It is preferred that each group 92, 94 of LEDs 84 contain at least ten LEDs 84. However, the system 70 can include more or fewer LEDs within a particular group depending upon a desired implementation of the system 70. Furthermore, the system 70 can include more or fewer groups of LEDs in the LED array 85.

With continuing reference to FIG. 9, there are four groups 92 of LEDs 84 located about the corner regions 96 of the LED array 85. Most preferably, at least fifteen LEDs 84 are disposed in each corner region 96 of the LED array 85. There are preferably four groups 94 of LEDs 84 disposed in lateral regions 98 of the LED array 85. Each lateral region 98 is located substantially between each corner region 94. Most preferably, at least ten LEDs 84 are disposed in each lateral region 98 of the LED array 85.

As described above, the LED array 85 is most preferably disposed on circuit board 86. In conjunction with the control system 90, the circuit board 86 includes control circuitry that controls the activation of one or more LEDs 84 within a particular group or groups 92, 94 of LEDs 84 in the LED array 85. As shown in the block diagram of FIG. 11, a power source 88 and a control system 90, such as a microprocessor or similar control device, are electrically connected to the circuit board 86. It will be appreciated that is also possible to control the LEDs without using a control system 90, that is, power source 88 can be switched "on" or "off" to activate and deactivate the LED array 85. It will be appreciated that pulse modulation techniques can also be used in conjunction with power source 88 to activate and deactivate one or more of the LEDs 84 in the LED array 85 according to a preferred duty cycle, herein defined as the LED "on" time relative to the LED "off" time.

Figure 11:
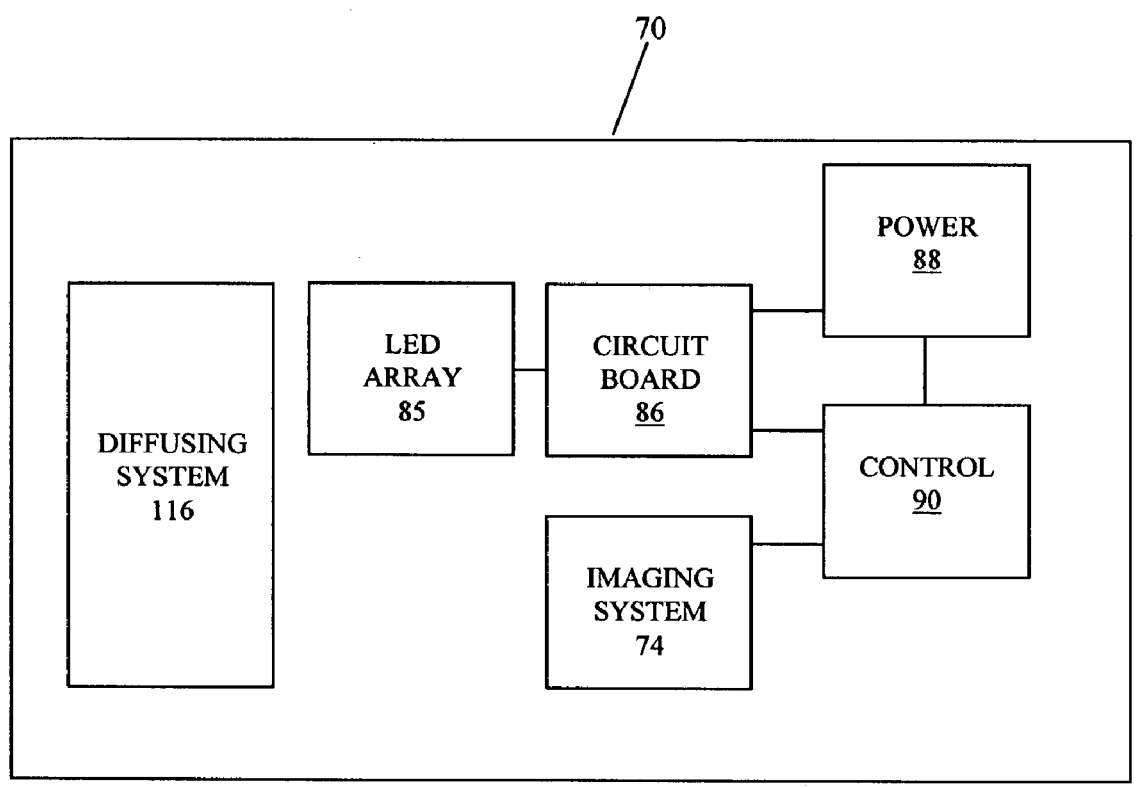
FIG. 11 is block diagram of an imaging system.

As shown in the block diagram of FIG. 11, in a preferred embodiment of the imaging system 70, the LED array 85 is electrically connected via circuit board 86 to the power source 88 and control system 90. The control system 90 includes control features for controlling the LED array 85 to emit infrared light toward an object 71. As described herein, the control system 90 can enable one or more of the LEDs 84 in a group or groups of the LED array 85 to emit light continuously or intermittently. That is, one LED 84 or a plurality of LEDs 84 can be selected and controlled to emit infrared light intermittently or continuously toward the object 71. Thus, the system 70 can be configured to transmit infrared light from the LED array in various permutations and combinations of LEDs 84 and/or LED groups 92, 94.

Referring now to FIG. 10, a first diffusion layer 100 is disposed adjacent to the emitting surfaces 102 of the LEDs 84 in the LED array 85. According to a preferred embodiment, the first diffusion layer 100 is glued, such as using known adhesives, onto the emitting surfaces 102 of the LED array 85, thereby operating to diffuse the light emitted by one or more LEDs 84 in the LED array 85. The first diffusion layer 100 is most preferably a holographic twenty degree diffuser, such as a product having identification code LSD20PC10-F10×10/PSA, manufactured by Physical Optics Corporation of Torrance, Calif. Most preferably, the first diffusion layer 100 has a length of about three and one-half inches, a width of about three and one-half inches, and a thickness of about 0.10 inches. When one or more of the LEDs 84 in the LED array 85 are activated, the first diffusion layer 100 diffuses the infrared light emitted from the LED array 85, thereby providing a first amount of diffusion to the emitted infrared light.

The interior surfaces 104 of the housing 72 are shown in FIG. 10. Most preferably, the interior surfaces 104 are coated with a reflective coating, such as white paint or the like, which reflects and further diffuses the already diffuse light produced by the first diffusion layer 100. With continuing reference to FIG. 10, a second diffusion layer 106 is spaced apart from the first diffusion layer 100 by a distance LDD. Most preferably, the distance LDD between the first and second diffusion layers 100 and 106 is about three inches. The second diffusion layer 106 is most preferably a holographic twenty degree diffuser, similar to or the same as the above-described first diffusion layer 100. The second diffusion layer 106 has a preferred length of about three and one-half inches, a width of about three and one-half inches, and a thickness of about 0.10 inches.

The second diffusion layer 106 further diffuses the already diffuse light reflected from the interior surfaces 104 and provided by the first diffusion layer 100. As shown in FIG. 8, the first and second diffusion layers are substantially planar, that is, the layers 100 and 106 each define a planar geometry. According to the most preferred embodiment, the planes defined by the first and second diffusion layers 100 and 106 are substantially parallel with respect to one another. The preferred parallel planar arrangement of the diffusion layers 100, 106 tends to promote a quantifiable and uniform amount of diffuse light emanating from the system 70 when one or more of the LEDs 84 are enabled.

With continuing reference to FIG. 10, a backing material 108, such as LUCITE; is disposed adjacent to the second diffusion layer 106. Most preferably, the backing material has a thickness of about 0.125 inches. A visible polarizer 110 is disposed adjacent to the backing material 108. The visible polarizer 110 is most preferably manufactured by Visual Pursuits of Vernon Hills, Ill. under part number VP-GS-12U, and having a thickness of about 0.075 inches.

Thus, the system 70 is operable to produce various levels of diffusion as the emitted light progresses through the first diffusion layer 100, reflects off of the interior surfaces 104 of the first compartment 72a, and continues to progress through the second diffusion layer 106, backing material 108, and polarizer 110. Thus, a level of diffusion results after the emitted light passes through the first diffusion layer 100. Another level of diffusion results from the reflection from the interior surfaces 104 of the first compartment 72a of the already diffused light provided by the first diffusion layer 100. Yet another level of diffusion results after the diffuse light passes through the second diffusion layer 106.

As shown in FIG. 8, the visible polarizer 110 preferably includes a central portion 112, most preferably in the shape of a circle having about a one-inch diameter. The central portion 112 geometry most preferably coincides with the shape and dimension of the camera lens 75. The polarization of the central portion 112 is preferably rotated approximately ninety degrees with respect to the polarization of the surrounding area 114 of the polarizer 110. In the preferred embodiment, the camera lens 75 contacts the backing material 108. As shown in FIG. 8, the positional location of the lens 75 within the housing 70 preferably coincides with or shares the same central axis as the central portion 112 of the polarizer 110. The central portion 112 of the polarizer 110 coinciding with the front of the lens 75 tends to remove any surface glare in the resulting camera image.

As shown in FIG. 10, the backing material 108 and the visible polarizer 110 have planar surfaces which preferably include a similar planar orientation with respect to the planes defined by the first and second diffusion layers 100, 106. According to a most preferred embodiment, the first diffusion layer 100, interior surfaces 104, second diffusion layer 106, backing material 108, and visible polarizer 110 define a diffusing system 116 (FIG. 10) for providing diffuse light to an object 71. It will be appreciated that the diffusing structure can include more or fewer components and the invention is not to be limited by any specific examples or embodiments disclosed herein. For example, the diffusing system 116 can include either the first or the second diffusion layers 100, 106, with or without the polarizer 110, or can include the first and second diffusion layers 100, 106 without the polarizer 110.

Once actuated, the system 70 operates to transmit diffuse light 80 toward an object 71 and produce a video image of the object 71 with the imaging system 74, as described above. More particularly, once the power source 88 is enabled, one or more of the LEDs 84 in the LED array 85 emit infrared light from the emitting surface(s) 102. The first diff-usion layer 100 provides a first amount of diffusion to the emitted infrared light. The interior surfaces 104 further diffuse the diffuse light emanating from the first diffusion layer 100. The second diffusion layer 106 further diffuses the already diffuse light which is then transmitted through the backing material 108 and the polarizer before illuminating the object 71. As described above, the object 71 reflects the emitted diffuse light 80 producing diffuse reflected light 82 that is captured by the imaging system 74. The imaging system 74 then produces a video image of the object 71. Accordingly, by emitting diffuse light according to a unique diffusion providing system 70, the system 70 aids in locating and differentiating between different material properties of the object 71, such as between blood vessels and tissue.

It is contemplated, and will be apparent to those skilled in the art from the preceding description and the accompanying drawings that modifications and/or changes may be made in the embodiments of the invention. For example, the planes defined by the first or second diffusing layers 100 and 106 can be adjusted to not be parallel with respect to one another, thereby providing different levels of diffuse light from the system 70. Furthermore, the plane defined by the LED array 85 is most preferably in substantial parallel relation with respect to the plane defined by the first diffusing layer 100. However, the planes defined by LED array 85 and the first diffusing layer 100 can be varied to accommodate various operational conditions, as will be appreciated by those skilled in the art. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. An apparatus to enhance the visibility of a buried structure beneath the surface of an object, the apparatus comprising:
   an illumination source for illuminating the buried structure wherein said illumination source emits diffuse infrared light;
   an imaging device for receiving diffuse light reflected from the object and for producing an image; and
   a video projector for projecting a visible light image of the buried structure onto the surface of the object, wherein the received diffuse light reflected from the object is coaxial with the projected visible light image.

2. The apparatus of claim 1 further comprising:
   a diffusing structure having more than one diffusing stage providing levels of diffusion to light emitted by the illumination source.

3. The apparatus of claim 2 wherein the diffusing structure has a first diffusing layer disposed adjacent the illumination source.

4. The apparatus of claim 3 wherein the first diffusing layer further comprises a holographic diffuser.

5. The apparatus of claim 4 wherein the diffusing structure further has a second diffusing layer providing a second level of diffusion to the light emitted by the illumination source.

6. The apparatus of claim 5 wherein the second diffusing layer has a holographic diffuser.

7. The apparatus of claim 5 wherein the second diffusing layer is spaced apart from the first diffusing layer.

8. The apparatus of claim 5 wherein the first diffusing layer has a first planar surface and the second diffusing layer has a second planar surface.

9. The apparatus of claim 8 wherein the first and second planar surfaces of the first and second diffusing layers are substantially parallel.

10. The apparatus of claim 1 Thither comprising:
    an illumination source, said source for emitting light toward the buried structure; and
    a polarizer for polarizing the light emitted by the illumination source.

11. The apparatus of claim 10 wherein the polarizer further comprises first and second regions wherein the first region provides a first polarization rotation and the second region provides a second polarization rotation that is different from the first polarization rotation.

12. The apparatus of claim 11 wherein the first and second polarization rotations differ by about ninety degrees.

13. The apparatus of claim 1 further comprising an array illuminating the buried structure from a range of different illumination directions.

14. An apparatus for imaging a body tissue to enhance visibility of subcutaneous blood beneath a surface of the body tissue, the apparatus comprising:
    a light source for providing diffuse infrared light to the body tissue;
    an imaging device for receiving light reflected from the body tissue, the imaging device being operable to provide an image of subcutaneous blood based on the reflected light; and
    a video projector for projecting a visible light image of subcutaneous blood, onto the surface of the body tissue, wherein the received diffuse light reflected from the object is coaxial with the projected visible light image.

15. The apparatus of claim 14 further comprising:
    a first diffusing layer positioned to intercept light from the light source, the first diffusing layer providing a first amount of diffusion to light emitted by the light source, the first diffusing layer having a first diffusing plane;
    a second diffusing layer spaced apart from the first diffusing layer, the second diffusing layer providing a second amount of diffusion to the light diffused by the first diffusing layer, the second diffusing layer having a second diffusing plane.

16. The apparatus of claim 15 wherein the first and second diffusing layers comprise holographic diffusers.

17. The apparatus of claim 15 wherein the first and second diffusing planes are substantially parallel.

18. The apparatus of claim 15 further comprising a polarizer for polarizing the light emitted by the light source.

19. The apparatus of claim. 15 wherein the light source further comprises groups of light emitting diodes arranged in a select pattern.

20. An apparatus to enhance visibility of a buried structure beneath a surface of an object, the apparatus comprising:
    groups of light-emitting diodes (LEDs), arranged in a select pattern which define an LED plane, illuminating the buried structure with diffuse infrared light;
    an imaging device for receiving diffuse light reflected from the object and for producing an image; and
    a video projector for projecting a visible light image of the buried structure onto the surface of the object, wherein the received diffuse light reflected from the object is coaxial with the projected visible light image.

21. The apparatus of claim 20 wherein the groups of LEDs are symmetrically arranged about the LED plane, and a first group of LEDs are adjacently located to plane corners of the LED plane and a second group of LEDs are located between adjacent plane corners of the LED plane.

22. The apparatus of claim 21 comprising a diffusing structure positioned to intercept and diffuse the light emitted from one or more of the LEDs.

23. The apparatus of claim 22 further comprising a diffusing layer having a diffusion plane, the diffusing layer located adjacent to the emitting surfaces of the LEDs, wherein the diffusion plane and the LED plane are substantially parallel.

24. An imaging system for viewing an object under illumination to enhance the visibility of a buried structure beneath the surface of the object, the imaging system comprising;
- an illumination source, said illumination source for emitting infrared light from a range of different illumination directions, to provide diffuse infrared light to the object;
- an imaging device for receiving the diffuse infrared light reflected from the object, and for generating an image of the buried structure; and
- a video projector for projecting a visible light image of the buried structure, onto the surface of the object, wherein the received diffuse light reflected from the object is coaxial with the projected visible light image.

25. A method for imaging a body tissue with light to enhance visibility of subcutaneous blood beneath the surface of the body tissue comprising the steps of:
- illuminating the body tissue with infrared light from a range of different illumination directions to provide diffuse infrared light to subcutaneous blood, wherein said diffuse infrared light has a wavelength that is absorbed by subcutaneous blood;
- generating an image of said subcutaneous blood beneath surface of the body tissue based on the diffuse infrared light reflected from the body tissue; and
- projecting said image onto the surface of the body tissue to enhance visibility of subcutaneous blood, wherein the projection of said image is properly aligned such that said reflected diffuse light is coaxial with the projected image, resulting in die projected image accurately overlaying the corresponding subcutaneous blood.

26. A method to enhance the visibility of a buried structure beneath the surface of an object, comprising the steps of:
- illuminating an object with diffuse infrared light;
- producing a visible light image of said buried structure beneath the surface of said object with said diffuse light reflected from said buried structure; and
- projecting said a visible light image of said buried structure onto the surface of the object to enhance the visibility of the buried structure beneath the surface of the object, wherein the projection of said visible light image is properly aligned such that said reflected diffuse light is coaxial with the projected visible light image, resulting in the projected visible light image accurately overlaying the corresponding buried structure.

* * * * *

UNITED STATES PATENT AND TRADEMARK OFFICE
CERTIFICATE OF CORRECTION

PATENT NO. : 7,239,909 B2 Page 1 of 1
APPLICATION NO. : 10/386249
DATED : July 3, 2007
INVENTOR(S) : Herbert D. Zeman and Gunnar Lovhoiden It is certified that error appears in the above-identified patent and that said Letters Patent is hereby corrected as shown below:

On the title page, item:
second line under heading, Zeman, should read:

Zeman et al.

Item    (75) Inventor: Herbert D. Zeman, Memphis, TN (US), should read:

(75) Inventors: Herbert D. Zeman, Memphis, TN (US)
        Gunnar Lovhoiden, Bartlett, TN (US)

Item    (74) Attorney, Agent, or Firm - Butler, Snow, O'Mara,
    Stevens & Canada, PLLC should read:

(74) Attorney, Agent, or Firm - Butler, Snow, O'Mara,
    Stevens & Cannada, PLLC Signed and Sealed this Second Day of February, 2010

David J. Kappos
*Director of the United States Patent and Trademark Office*